United States Patent [19]

Priel et al.

[11] Patent Number: 5,422,344
[45] Date of Patent: Jun. 6, 1995

[54] METHOD OF TREATING RETROVIRAL INFECTIONS IN MAMMALS

[75] Inventors: Esther Priel, Beer Sheva, Israel; Donald G. Blair, Kensington; Stephen D. Showalter, Frederick, both of Md.

[73] Assignee: The United States of America as represented by the Secretary of the Department of Health & Human Services, Washington, D.C.

[21] Appl. No.: 520,456

[22] Filed: May 8, 1990

[51] Int. Cl.$^6$ ............................................. A61K 31/70
[52] U.S. Cl. ........................................ 514/50; 514/410
[58] Field of Search .................................. 514/50, 410

[56] References Cited

PUBLICATIONS

Schreiber et al CA; 110:57987w 1989.
Foglesong CA, 95:56996h 1981.
Liu et al CA, 93:2764w 1980.
Civitico et al CA, 113:144906z (1991).
Civitico et al. (1990) Journal of Medical Virology, 31:90-97.
Giovanella et al, Science, vol. 246, pp. 1046–1048, 1983.
Hutchinson, Tetrahedron, vol. 37, pp. 1047–1065, 1981.
Lock et al., Anti–Cancer Drug Design, 1987, vol. 2, pp. 151–164.
Mitsuya et al, Proceedings of the National Academy of Sciences, vol. 82, pp. 7096–7100, Oct. 1985.
Priel et al, Abstracts of the Fifth International Conference on Aids, 1989, p. 586.
Snapka, Molecular and Cellular Biology, Dec. 1986, pp. 4221–4227.
Stewart et al., Cell, vol. 60, pp. 141–149, Jan. 12, 1990.
Wall et al, Journal of the American Chemical Society, vol. 88, p. 16, Aug. 20, 1966.
Weis et al., Virology, vol. 114, pp. 563–566, 1981.
"Yeast DNA Topoisomerases and Their Structural Genes," M. Yanagida et al., *Nucleic Acids and Molecular Biology*, vol. 1, pp. 196–209, 1980.
"Unraveling Retrovirus Integration," D. Gradgenett et al., *Cell*, vol. 60, Jan. 12, 1990, pp. 3–4.
"Correct Integration of Retroviral DNA in Vitro," P. Brown et al., *Cell*, vol. 49, pp. 347–356 1989.
"Retroviral integration: Structure of the initial covalent product and its precursor, and a role for the viral IN protein," Brown et al., *Proc. Natl. Acad. Sci. USA*, vol. 86, pp. 2525–2529, Apr. 1989.
"Integration of mini–retroviral DNA: . . . retroviral integration," Fujiwara et al., *Proc. Natl. Acad. Sci. USA*, vol. 86, pp. 3065–3069, May 1989.
"RNA Tumor Viruses," Weiss et al., Cold Spring Harbar Laboratory, 1982, pp. 392–393.
"RNA–Directed DNA Synthesis and RNA Tumor Viruses," Temin et al., *Advances in Viral Research*, vol. 17, pp. 129–155, 1983.

*Primary Examiner*—Raymond Henley, III
*Assistant Examiner*—Russell Travers
*Attorney, Agent, or Firm*—Birch, Stewart, Kolasch & Birch

[57] ABSTRACT

The present invention is directed to the use of pharmaceutical compositions, containing an effective amount of topoisomerase I inhibitor such as camptothecin, useful in blocking both the initiation of infection and replication of retroviruses in host cells, thus reducing and eliminating retroviral production in infected cells. Use of such inhibitors provides as means of reducing or eliminating retroviral infections and their deleterious consequences in infected humans and animals.

8 Claims, 2 Drawing Sheets

METHOD OF TREATING RETROVIRAL INFECTIONS IN MAMMALS

BACKGROUND OF THE INVENTION

1. Field of the Invention

The present invention relates to a method of treating retroviral infections in mammals via the use of camptothecin (CPT) and similar compounds which act as inhibitors of retroviral topoisomerase I, blocking the initiation of retroviral infection and replication in target cells and reducing and eliminating viral production by cells infected with such viruses, thereby reducing or eliminating the viral infection and its consequences in infected individuals. As a consequence of this mechanism of action, these compounds should find wide utility in both human and veterinary medicine.

2. Description of Related Art

Weis et al. ((1981) *Virology* 114: 563–66) have described the detection of DNA topoisomerase activity associated with the Prague C strain of Rous Sarcoma Virus. The enzyme activity was partially purified from viral extracts using standard biochemical techniques, and compared to the chicken cellular topoisomerase. Both showed identical behavior in response to different concentrations of magnesium, and both were indistinguishable with respect to size (40,000–60,000 daltons) upon glycerol gradient centrifugation. The authors concluded that the "viral" enzyme most probably represented non-specific incorporation of the cellular topoisomerase into the viral particle. The exact nature of the topoisomerase was not further analyzed, and the authors indicated that its role in the retroviral life cycle was indeterminant. The conclusion that the viral enzyme was a cellular contaminant, however, would imply a non-essential role.

Snapka ((1986) *Mol. Cell. Biol.* 6: 4221–27) reported that camptothecin selectively interferes with Simian Virus 40 DNA replication.

The use of camptothecin and similarly acting compounds for treating retrovirus infections has yet to be reported.

SUMMARY OF THE INVENTION

The clinical importance of human immunodeficiency virus (HIV) has led to intensive attempts to identify specific inhibitors. One basis for the development of anti-HIV drugs is an increased understanding of the retroviral life cycle and of the proteins and enzymes involved in HIV replication.

In contrast to Weis et al., discussed above, the present inventors have identified a topoisomerase activity associated with two lentiviruses which is clearly distinguishable from the cellular topoisomerases found in the cells in which the viruses were grown. In particular, the response of the cellular and viral topoisomerases to $Mg^{2+}$ is clearly different (Priel et al., in preparation), whereas the Rous viral associated enzyme of Weis et al. was indistinguishable from cellular topoisomerase with respect to its $Mg^{2+}$ dependence. The identification of the lentivirus associated topoisomerase as a topoisomerase I type activity was not suggested by Weis et al., but was demonstrated by camptothecin inhibition. The unique properties of the HIV and EIAV-associated activities suggested a specific viral association and thus a possible role in the life cycle of these viruses which was not suggested by Weis et al. The genomic structure of lentivirus and C-type retroviruses is clearly different, and the life cycle of the lentiviruses is subject to a number of complex levels of control at both the RNA and protein levels. It is not obvious that the presence of a contaminating cellular enzyme in one (RSV) would indicate that the same would be true for the other (HIV-/EIAV), nor would the role of topoisomerase I necessarily be the same in the two cases. The observation that the lentivirus-associated topoisomerase activity was specific and unique, and that CPT inhibited this activity, was novel, and was the first suggestion that a topoisomerase inhibitor might function as an inhibitor of lentivirus replication.

The results described here are distinguishable from the selective camptothecin interference with Simian virus 40 DNA replication reported by Snapka, supra, as Simian virus is a DNA virus, while the retroviruses with which the present invention is concerned are RNA viruses. The two types of viruses share no homology between their lifecycles or mechanisms of nucleic acid replication. Furthermore, it is the applicants discovery and the basis of the present invention that topo I plays a role in the lifecycle of retroviruses. Thus, the experimental results of Snapka could not have served as a basis for predicting the efficacy of camptothecin in the treatment of retroviral infections, as described below.

It has been discovered that a novel topoisomerase I (topo I) activity is present in HIV-1, equine infectious anemia virus (EIAV), and Moloney murine leukemia virus (MoMuLV). This topo I activity is present in purified EIAV cores, and is associated with the EIAV p11 nucleocapsid protein. The viral associated topo I possesses characteristics different from those of the host cell enzymes. While cellular topo I has been implicated in DNA replication and transcription (Zhang et al. (1982) *Proc. Natl. Acad. Sci. USA* 85: 1060–64), it was not previously known if the viral associated topo I had a role in the virus life cycle.

As shown below, this viral associated topo I activity is inhibited by camptothecin (CPT), a known specific inhibitor of eukaryotic topo I (Gupta et al. (1988) *Cancer Res.* 48: 6404–10). Camptothecin is a cytotoxic alkaloid isolated from Camptotheca acuminata, and has strong antitumor activity against a wide range of experimental tumors and human colon cancer. In its cytotoxic doses, CPT inhibits RNA and DNA synthesis and causes rapid and reversible fragmentation of DNA in mammalian cells (Wall et al. (1986) *J. Am. Chem. Soc.* 88: 3888–90, herein incorporated by reference in its entirety). These pleiotropic effects were shown to be mediated via a single cellular target-topo I.

Accordingly, it is an object of the present invention to provide a method for treating retroviral infections in a mammal, including humans, which comprises administering to the subject an anti-retroviral effective amount of a topoisomerase I inhibitor such as camptothecin or derivatives thereof.

A further object of the present invention is to provide a method for treating retroviral infections in a mammal, including humans, which comprises administering to the subject an anti-retroviral effective amount of a topoisomerase I inhibitor and an anti-retroviral effective amount of a compound such as AZT, soluble CD4, or an interferon (e.g., α-, β-, or γ- interferon), or combinations of these latter compounds.

Yet a further object of the present invention is to provide a pharmaceutical composition comprising an anti-retroviral effective amount of a topoisomerase I inhibitor and an anti-retroviral effective amount of AZT, soluble CD4, or an interferon, or combinations of these latter compounds.

These objects and others are accomplished in accordance with the present invention by administering an anti-retroviral effective amount of a pharmaceutical composition containing a topoisomerase I inhibitor. Representative topoisomerase I inhibitors useful in treating retroviral infections include camptothecin and derivatives thereof which are topoisomerase I inhibitors. Representative derivatives of camptothecin which can be employed in the present method are described in Giovanella et al. (1989) Science 246: 1046–48 and Jaxel et al. (1989) Cancer Res. 49: 1465–69, the contents of which are herein incorporated by reference in their entireties.

These compounds are listed below:

Camptothecin

| Compound | Camptothecin derivative |
|---|---|
| 1 | S. |
| 2 | R. |
| 3 | RS— |
| 4 | 20-Deoxy-RS— |
| 5 | 21-Lactam-S |
| 6 | Tricyclic-RS— |
| 7 | 10-Hydroxyl-S— |
| 8 | 11-Hydroxyl-RS— |
| 9 | 10-Et$_2$N—CH$_2$CH$_2$—O—S— |
| 10 | 10,11-(CH$_2$O)$_2$—RS— |
| 11 | 10,11-OCH$_2$O—RS— |
| 12 | 9-NH$_2$—S— |
| 13 | 10-NH$_2$—RS— |
| 14 | 11-NH$_2$—RS— |
| 15 | 12-NH$_2$—S— |
| 16 | 9-NH$_2$-20-OCOCH$_2$NH$_3$+ —RS— |
| 17 | 11-CN—RS— |
| 18 | 9-NO$_2$—S— |
| 19 | 9-NO$_2$—RS— |
| 20 | 10-NO$_2$—RS— |
| 21 | 11-NO$_2$—RS— |
| 22 | 12-NO$_2$—S— |
| 23 | 20(RS)-9-amino- |
| 24 | 20(RS)-10-amino- |
| 25 | 20(RS)-10,11-Methylenedioxy |
| 26 | Sodium salt of 20(RS)-10,11-Methylenedioxy |
| 27 | CPT11: 7-ethyl-10-[4-(1-piperidino)-1-piperidino]carbonyloxy |

A number of agents, e.g., AZT, soluble CD4, and interferons, are known to block HIV infection either at the cell surface or at the level of reverse transcriptase, thus preventing the early stages of the HIV infections process. Other agents, such as interferon α, have been reported to suppress HIV expression in chronically infected cell lines. The present invention, i.e., the use of camptothecin to inhibit retroviral infection, offers the advantage of acting to block the initiation of new rounds of retroviral infection and replication in host cells using a target different from reverse transcriptase, thereby reducing or eliminating the viral infection and its consequences in the infected individual. This drug provides the opportunity to employ multiple drugs with different targets in order to maximize the inhibition of virus growth and subsequent disease induction. Thus, a topoisomerase I inhibitor may be administered concomitantly with any one, or a combination, of the compounds listed above. Use of topo I inhibitors also provides a means of blocking and controlling other retroviral diseases in man or animals since such compounds have the ability to interfere with both type C retroviruses as well as lentiviruses. Such properties portend a wide activity and utility in both human and veterinary medicine.

The activity of camptothecin in inhibiting the initiation of infection by type C retroviruses (e.g., Moloney MuLV) and lentiviruses (e.g., HIV and EIAV) in cell culture has been demonstrated. It is expected that camptothecin and other topoisomerase I inhibitors will be active in vitro and in vivo against other retroviruses. The compounds of the invention have been shown to exhibit little or no cytotoxicity at low dosages.

The compounds of the present invention can be used for the treatment and/or prophylaxis of human and animal diseases, particularly mammalian diseases, caused by the above-mentioned viruses and other retroviruses. It is contemplated that the invention compounds will be formulated into a pharmaceutical composition comprising an effective antiviral amount of the compound and a pharmaceutically acceptable carrier. An effective antiviral amount of the pharmaceutical composition will be administered to the subject, human, animal, or mammal, in a manner which inhibits or prevents viral infection or replication. The amount of the compound and the specific pharmaceutically acceptable carrier will vary depending upon the host and its condition, the mode of administration, and the type of viral condition being treated.

In a particular aspect, the pharmaceutical composition comprises a topoisomerase I inhibitory compound in effective unit dosage form. As used herein, the term "effective unit dosage" or "effective unit dose" is denoted to mean a predetermined antiviral amount sufficient to be effective against the viral organisms in vivo. Pharmaceutically acceptable carriers are materials useful for the purpose of administering the medicament, which are preferably non-toxic, and may be solid, liquid, or gaseous materials, which are otherwise inert and medically acceptable, and are compatible with the active ingredients. The pharmaceutical compositions may contain other active ingredients such as antimicrobial agents and other agents such as preservatives.

These pharmaceutical compositions may take the form of a solution, emulsion, suspension, ointment, cream, granule, powder, tablet, capsule, sachet, lozenge, ampoule, pessary, or suppository. They may be administered parenterally, intramuscularly, subcutaneously, intravenously, intraarticularly, transdermally, orally, bucally, as a suppository or pessary, topically, as an aerosol, spray, or drops, depending upon whether the preparation is used to treat internal or external viral infections.

The compositions may contain the compound in an amount of from 0.1%–99% by weight of the total composition, preferably 1 to 90% by weight of the total composition. For intravenous injection, the dose may be about 0.01 mg to about 2.5 mg/kg/day. If applied topically as a liquid, ointment, or cream, the compound may be present in an amount of about 0.01 to about 100 mg/ml of the composition.

The compounds according to the invention may also be formulated for injection and may be presented in unit dose form in ampoules or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form for consitution with a suitable vehicle, e.g., sterile, pyrogen-free water, before use.

Alternatively for infections of external tissues, e.g., the mouth and skin, the compositions may be applied to the infected part of the body of the patient as a topical ointment or cream. The compounds may be presented in an ointment, for instance with a water soluble ointment base, or in a cream, for instance with an oil in water cream base, in a concentration of from about 0.1 to 10%, preferably 0.5 to 2.0%, most preferably 1.5%, w/v.

The compounds may also be applied into body orifices such as the rectum and vagina in the form of a suppository or cream.

For systemic administration, the daily dosage as employed for adult human treatment will range from about 0.01 mg/kg to about 2.5 mg/kg which may be administered in a single dose or daily over a 5 day course, depending on the route of administration (e.g., intravenous infusion) and the condition of the patient.

Further scope of the applicability of the present invention will become apparent from the detailed description and drawings provided below. However, it should be understood that the detailed description and specific examples while indicating preferred embodiments of the invention are given by way of illustration only since various changes and modifications within the spirit and scope of the invention will become apparent to those skilled in the art from this detailed description.

Figures 1A, 1B:
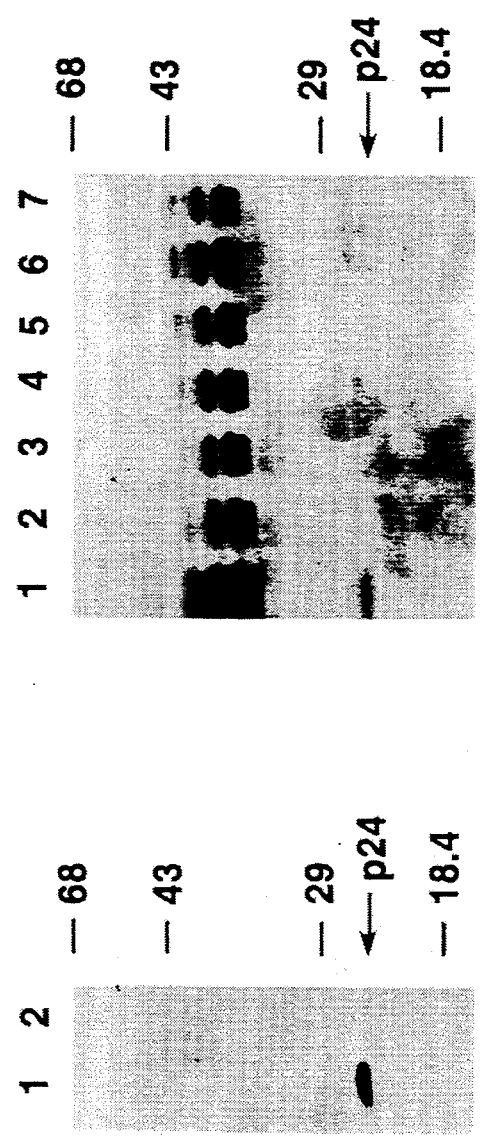
FIG. 1. Western blot analysis of HIV p24 antigen in supernatants and cell extracts following HIV infection and CPT treatment.

A. H9 cells were infected as described in Table 1 and the text. Virus was pelleted from culture supernatants 7 days after infection. The viral pellets were resuspended, lysed, and the proteins separated and transferred as described in the Examples. The blot was analyzed using an HIV p24 specific monoclonal antibody (S. Showalter and M. Zweig, unpublished), and visualized using the Bio-Rad immunogold kit. Lane 1: virus from untreated infected cells; lane 2: virus from cells treated with 0.005 $\mu$M CPT for the first 18 h after infection.

B. Extracts of HIV-infected cells (7 days post-infection) were prepared and analyzed as described in the Examples using an HIV p24 specific monoclonal antibody (S. Showalter and M. Zweig, unpublished). Blots were visualized using the Bio-Rad immunogold kit. Lane 1: untreated infected cells; lane 2: 0.2 $\mu$M CPT; lane 3: 0.1 $\mu$M CPT; lane 4: 0.05 $\mu$M CPT; lane 5: 0.02 $\mu$M CPT; lane 6: 0.01 $\mu$M CPT; lane 7: 0.005 $\mu$M CPT. All cells were exposed to drugs for 1 h at the time of exposure to HIV.

Figure 2:
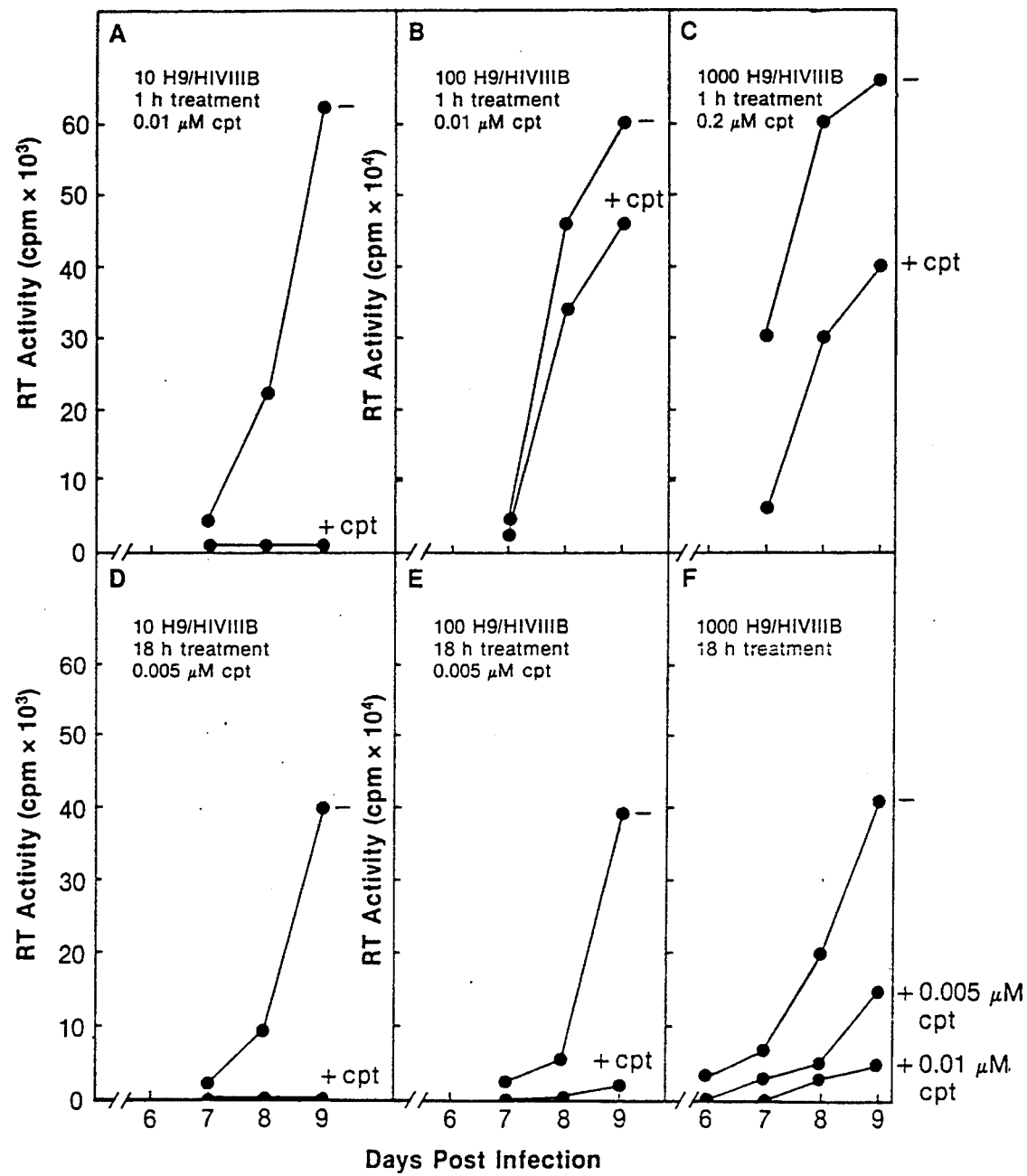

FIG. 2. Effect of CPT on HIV replication in cocultivation of H9/HIV chronically infected cells with H9 cells.

10 H9/HIV-IIIB (A,D), 100 H9/HIV-IIIB (B,E) or 1000 H9/HIV-IIIB cells (C,F) were cocultivated with $10^5$ H9 cells in the presence or absence of 0.01 $\mu$M (A,B), 0.2 $\mu$M (C), 0.005 $\mu$M (D,E), or 0.005–0.01 $\mu$M (F) of CPT for 1 h (A,B,C) or 18h (D,E,F). RT activity was measured in the culture media 7,8, and 9 days post-infection and treatment.

DESCRIPTION OF THE PREFERRED EMBODIMENTS

Virus Strain and Cells: H9 cells and an HIV-1-producing cell line, H9/HIV-IIIB, were grown in RPMI-1640 medium supplemented with 15% fetal bovine serum.

Compounds: Camptothecin (CPT), m-AMSA, and VP-16 were obtained from the Division of Cancer Treatment, Drug Synthesis and Chemistry Branch, National Cancer Institute. Stock solutions of the drugs at 10 mM in dimethyl sulfoxide (DMSO) were stored in aliquots at $-20°$ C.

HIV-Acute Infection of H9 Cells by HIV and Drug Treatment: One ml of culture supernatant of H9/HIV-IIIB cells ($10^6$/ml) was used after centrifugation (200xg, 20 min) and filtration (0.45 $\mu$m) for infecting $10^5$ H9 cells in the presence or absence of different levels of CPT, m-AMSA or VP-16. Control cells received equivalent volumes of DMSO. The cells were incubated for 1 h at 37° C., pelleted, washed and resuspended in fresh media. Reverse transcriptase (RT) activity in the culture media was measured seven, eight, and nine days after infection as described by Goff et al. (1981) *J. Virol.* 38: 239–48.

Cocultivation of H9/HIV-IIIB Cells with Uninfected H9 Cells and CPT Treatment: Ten, 100 or 1,000 H9/HIV-IIIB cells were cocultivated with $10^5$ H9 cells in the presence or absence of different CPT doses. Cells were incubated for 1 h at 37° C., pelleted, washed and resuspended in fresh media. RT activity in the culture media was measured seven, eight, and nine days after infections, as described above.

For a longer treatment period, H9/HIV-IIIB cells were cocultivated with H9 cells in the presence or absence of 0.005–0.01 $\mu$M CPT for 18 h at 37° C.

Western Blot Analysis.

The culture media from cells subjected to different treatments was prepared by centrifugation (200xg, 10 min) to remove whole cells and debris, the viral particles were subsequently pelleted (35,000 rpm, 1½h), and the viral pellet was resuspended in 100 $\mu$l of RIPA buffer (50 mM Tris-HCl, pH 7.5; 0.5M NaHPO$_4$, 0.5% NP40, 0.25% Na-deoxycholate, 0.1% SDS). Cell extracts were prepared by resuspending cells in RIPA buffer, and the supernatant was cleared from cell debris by centrifugation (30,000 rpm, 1 h). Protein concentration was determined using the Bio-Rad protein assay. Equal volumes of the total viral lysate or 100 $\mu$g of cellular proteins were electrophoresed in 10% SDS gels and electroblotted to nitrocellulose. Immunodetection was done with 1:200 dilution of HIV p24 monoclonal antibodies or HIV nef monoclonal antibodies using the immunoblot protein A gold assay (Bio-Rad).

EXAMPLE 1

CPT Inhibition of HIV Replication Following Acute Infection of H9 Cells with HIV-IIIB. In order to determine appropriate concentrations of CPT which would permit cell viability and growth while inhibiting viral infection or replication, H9 cells were infected with HIV-IIIB as described above in the absence or presence of different CPT doses. The cells were incubated for 1 h at 37° C., pelleted, washed and resuspended in fresh media. Reverse transcriptase (RT) activity in the culture media was measured seven days after infection. As shown in Table 1, there was a 98% inhibition of HIV-1 replication when 0.05–0.2 μM CPT was added during the infection processes. At this CPT dose, no effect on cell viability was detected using the trypan blue dye exclusion, but cell growth was arrested. Lower doses of CPT, 0.005–0.02 μM, had a similar inhibitory effect (89–93%) on HIV replication, and no effect on cell viability or cell growth was detected.

TABLE 1

Effect of Different CPT Doses on HIV Replication in Acute Infection of H9 Cells

| [CPT] μM | Cell No. | Cell Viability % | RT activity* cpm/cell $10^5$ | % Inhibition |
|---|---|---|---|---|
| 0 | $2.5 \times 10^6$ | 100 | 5529 ± 2299 (2) | |
| 0.2 | $1 \times 10^5$ | 100 | 139 ± 96 (2) | 98 ± 0.8 |
| 0.1 | $1 \times 10^5$ | 100 | 106 ± 30 (2) | 98 ± 0.2 |
| 0.05 | $1 \times 10^5$ | 100 | 235 ± 62 (3) | 96 ± 1.5 |
| 0.02 | $4 \times 10^5$ | 100 | 400 ± 103 (3) | 93 ± 2 |
| 0.01 | $2.2 \times 10^6$ | 100 | 528 ± 40 (3) | 89 ± 4 |
| 0.005 | $2 \times 10^6$ | 100 | 429 ± 116 (3) | 89 ± 4 |

*The RT activity was measured 7 days post-infection and treatment. All data presented are means (± standard deviation) from two to three independent experiments.

The reduction in HIV production following CPT treatment was confirmed by analyzing virus particles pelleted from the culture media, lysed, separated by electrophoresis, and assayed by Western blot analysis using HIV p24 monoclonal antibodies. p24 was present in the culture media 7 days post-infection of H9 cells with HIV-IIIB (FIG. 1A, lane 1), but could not be detected in the culture media of H9 cells treated with CPT during HIV infection (FIG. 1A, lane 2). Moreover, p24 could not be detected in extracts from these CPT treated cells, while it was present in cell extracts from infected, untreated cells (FIG. 1B). These results are compatible with the reverse transcriptase results and indicate that CPT added during viral infection prevents subsequent HIV replication. The results suggest that the inhibitory effect of CPT on HIV replication is due to its effect on virus replication, and is not a result of its cytotoxic character. Moreover, the anti-HIV CPT doses are 400 times lower than the cytotoxic doses (data not shown). These results also indicate that a 1 hour exposure to CPT during viral infection was sufficient to prevent HIV replication. Measurement of RT activity released into the culture media 8 and 9 days after infection and CPT treatment (Table 2) indicates that at 0.05 μM CPT, essentially complete inhibition of HIV production is observed. However, at lower doses of CPT (0,005–0.02 μM), less complete inhibition was observed, and by 9 day's after infection and CPT treatment, the treated cells were producing between 48 and 83% of control levels of RT activity. The increasing levels of RT activity observed by 9 days after infection could be due to virus spread in the absence of the drug from a small number of infected cells.

TABLE 2

DETERMINATION OF HIV REPLICATION IN ACUTE INFECTION OF H9 CELLS FOLLOWING 1 HOUR TREATMENT WITH DIFFERENT CPT DOSES

| | Days After Infection | | | | | |
|---|---|---|---|---|---|---|
| | 7 | | 8 | | 9 | |
| [CPT] μM | RT/Cell cpm/$10^5$ Cell | (% Inhibition) | RT/Cell cpm/$10^5$ Cell | (% Inhibition) | RT/Cell cpm/$10^5$ Cell | (% Inhibition) |
| 0 | 32318 | (0) | 134224 | (0) | 136762 | (0) |
| 0.05 | 0.03 | (100) | 1.5 | (100) | 9.4 | (100) |
| 0.02 | 29.7 | (100) | 325 | (98.8) | 65761 | (52) |
| 0.01 | 5085 | (85) | 33968 | (75) | 112870 | (17) |
| 0.005 | 5400 | (84) | 34268 | (74) | 102450 | (24) |

To examine the relative sensitivity of RT production at 9 days to the number of initially infected cells, 10, 100 or 1000 H9/HIV-IIIB infected cells were mixed with $10^5$ H9 uninfected cells, and RT activity was measured in the culture media 7, 8, and 9 days post-infection. As can be seen from Table 3, the same RT activity was observed 8 and 9 days post-infection when 100 or 1000 H9/HIV-IIIB cells were cocultivated with H9 uninfected cells. These results indicate that under these assay conditions, the presence of 100 infected cells in the cell culture was sufficient to obtain the maximum RT activity in the culture media 9 days later. This suggests that the relative efficiency of CPT at blocking the establishment of HIV infection may actually be more efficient than indicated by the results in Tables 1 and 2.

TABLE 3

DETERMINATION OF HIV REPLICATION IN COCULTIVATION OF H9 CELLS WITH H9/HIV-IIIB CHRONICALLY INFECTED CELLS

| Days Post-infection | H9 Cells | H9/HIV-IIIB Cells | RT Activity* cpm/$10^6$ Cells |
|---|---|---|---|
| 6 | $10^5$ | 10 | 156 ± 10 |
| | | 100 | 13570 ± 520 |
| | | 1000 | 38900 ± 1560 |
| 7 | $10^5$ | 10 | 1393 ± 460 |
| | | 100 | 83056 ± 2600 |
| | | 1000 | 181804 ± 5120 |
| 8 | $10^5$ | 10 | 6461 ± 620 |
| | | 100 | 121417 ± 4000 |
| | | 1000 | 134553 ± 11250 |
| 9 | $10^5$ | 10 | 16005 ± 2500 |
| | | 100 | 82868 ± 3250 |
| | | 1000 | 94955 ± 4500 |

*All data presented are means (±SD) from three different experiments.

EXAMPLE 2

Topo II Inhibitors m-AMSA and VP-16 Do Not Affect HIV Replication Following Acute Infection of H9 Cells by HIV-IIIB. Since CPT is an anticancer drug and a known topo I inhibitor, its effects on HIV replication were compared to those of other anticancer drugs which are known to inhibit the related topoisomerase II enzyme. No effect on HIV replication was observed when non-cytotoxic doses of m-Amsa and VP-16 were added during HIV infection (Table 4). These results indicate that the effect of CPT on HIV replication is a specific phenomenon associated with its topo I inhibitory activity, and not a general property of all topoisomerase inhibitors.

serve as a useful agent for blocking retroviral induced disease, its ability to act in vivo had to be demonstrated.

TABLE 4

Effect of Different Doses of Topoisomerase II Inhibitors M-AMSA and VP-16 on HIV Replication

| | No Drug | | m-Amsa | | | VP16 | | |
|---|---|---|---|---|---|---|---|---|
| Days post-infect. | No. Cells | RT/Cell cpm/$10^5$ cells | [m-Amsa] $\mu M$ | No. Cells | RT/Cell cpm/$10^5$ cells | [VP16] $\mu M$ | No. Cells | RT/Cell cpm/$10^5$ cells |
| 6 | $5 \times 10^5$ | 18813 | 0.4 | $4 \times 10^5$ | 36070 | 0.5 | $1 \times 10^6$ | 26283 |
| | | | 1 | $4 \times 10^5$ | 32674 | 1.5 | $1 \times 10^6$ | 32242 |
| 7 | $8 \times 10^5$ | 23002 | 0.4 | $9 \times 10^5$ | 25372 | 0.5 | $1.6 \times 10^6$ | 26143 |
| | | | 1 | $7.5 \times 10^5$ | 40057 | 1.5 | $2 \times 10^6$ | 33626 |
| 8 | $1.1 \times 10^6$ | 33914 | 0.4 | $1.3 \times 10^6$ | 38594 | 0.5 | $2.4 \times 10^6$ | 29158 |
| | | | 1 | $1.1 \times 10^6$ | 45558 | 1.5 | $2.4 \times 10^6$ | 30675 |
| 9 | $1.5 \times 10^6$ | 46710 | 0.4 | $2 \times 10^6$ | 37556 | 0.5 | $3 \times 10^6$ | 25183 |
| | | | 1 | $2 \times 10^6$ | 36442 | 1.5 | $4 \times 10^6$ | 29194 |

EXAMPLE 3

CPT Inhibition of HIV Replication in Cocultivation of H9/HIV-IIIB Chronically Infected Cells with H9 Uninfected Cells. Since it is likely that HIV infection in vivo involves cell to cell contact and virus production by previously infected cells, the ability of CPT to block the spread of HIV in uninfected H9 cells cocultivated with cells chronically infected with HIV was examined. The results shown in FIG. 2A indicate that 100% inhibition of HIV replication was observed when 10 infected cells were mixed with uninfected cells in the presence of 0.01 $\mu M$ CPT for 1 h. This CPT dose inhibited 50% of the HIV replication when 100 infected cells were mixed with uninfected cells (FIG. 2B), and 13% inhibition was observed when 1000 infected cells were used (data not shown). However, increasing the CPT dose to 0.2 $\mu M$ reduced HIV replication to 15% of control values when 1000 infected cells were mixed with $10^5$ uninfected H9 cells (FIG. 2C). Cocultivation of 10 or 100 HIV chronically-infected cells with $10^5$ uninfected H9 cells in the presence of 0.005 $\mu M$ CPT for 18 h at 37° C. also inhibited 98–100% of HIV replication as measured by RT activity 7, 8, and 9 days after treatment (FIG. 2D,E). These results indicate that an increasing the amount of virus (more infected cells) can overcome the effects of a low CPT level, but that increasing CPT doses or more continuous exposure to the drug strongly inhibits HIV replication and spreading even when the initial dose of virus infected cells is increased.

EXAMPLE 4

INHIBITION OF FRIEND VIRUS DISEASE IN MICE BY CAMPTOTHECIN. In order for CPT to

The Friend virus/spleen focus forming virus (SFFV) mouse model was used to test CPT in vivo. SFFV is a defective type C retrovirus which induces the rapid onset of erythroleukemia, characterized by severe splenomegaly, and death of the affected animal within 3–6 weeks after innoculation. A well characterized stock of SFFV, in complex with an amphotropic murine C-type virus which induced only a low incidence of lymphoid and myloid disease after a long latency, was injected into adult mice at viral dilutions which would be expected to induce Friend erythroleukemia in essentially 100% of infected mice.

Male NFS mice were injected IP with 0.5 ml of virus stock to which CPT, disolved in DMSO, was added. The average weight of a mouse was 24 g, and CPT was added from a stock at 10 mg/ml. DMSO was added to A, E and I viral inoculum at 2.8%, the maximum level. Animals were sacrificed 4 weeks after inoculation, and spleens were weighed to determine the incidence of Friend virus induced splenomegaly. The results are shown in Table 5, and demonstrate that CPT reduced the number of mice showing enlarged spleens and the average spleen weight in comparison to control, virus infected mice.

TABLE 5

Inhibition of Friend Virus Disease in Mice by Camptothecin

| GROUP | VIRUS DIL. | CPT (mg/kg) | SPLEEN WEIGHT (g) | AVG. | NUMBER FRIEND DISEASE POSITIVE (SPLEEN WEIGHT >0.2 g) |
|---|---|---|---|---|---|
| A | 1/500 | 0 | 1.2, 1.4, 1.5, 1.5, 0.2 | 1.16 g | 4/5 |
| B | " | 5 | 0.1, 0.3, 1.0, 0.9, 1.6 | 0.78 | 4/5 |
| C | " | 10 | 0.7, 0.2, 1.3, 1.8, 0.2 | 0.84 | 3/5 |
| D | " | 20 | 0.3, 0.2, 0.3, 0.3, 0.3 | 0.28 | 4/5 |
| E | 1/2000 | 0 | 0.2, 0.2, 0.2, 2.4, 1.9 | 0.58 | 2/5 |
| F | " | 5 | 0.2, 0.3, 0.2, 0.2, 0.2 | 0.22 | 1/5 |
| G | " | 10 | 0.2, 0.2, 0.1, 0.2, 0.2 | 0.18 | 0/5 |
| H | " | 20 | 0.2, 0.2, 0.3, 0.2, 0.2 | 0.22 | 1/5 |
| I | NONE | 0 | 0.2, 0.1, 0.1, 0.1, 0.1 | 0.12 | 0/5 |
| J | " | 5 | 0.1, 0.2, 0.1, 0.1, 0.1 | 0.12 | 0/5 |
| K | " | 10 | 0.1, 0.1, 0.1, 0.1, 0.1 | 0.10 | 0/5 |
| L | " | 20 | 0.2, 0.1, 0.1, 0.1, 0.1 | 0.12 | 0/5 |

EXAMPLE 5

Inhibition of Disease Induction In Vivo by Spleen Focus Forming Virus (SFFV) by Intravenous or Intraperitoneal Infection of CPT. In a repeat and extension of the previous experiment, NFS mice were injected either intraperitoneally or intravenously with dilutions of infectious virus stock in the presence or absence of CPT. Virus was mixed with stocks of CPT dissolved in DMSO at 10 mg/ml and adjusted so that mice were treated at 20 mg/kg. In samples without CPT, DMSO was added to an equivalent concentration (9.6%). In both IP and IV injections, 0.5ml was injected per mouse. Animals were monitored and sacrificed 4 weeks after injection. Spleens were weighed, and a spleen weight in excess of 0.2 gm was judged positive for SFFV disease. The results summarized in Table 6 support the initial demonstration of the ability of CPT to block virus spread in vivo by multiple routes of infection, and further suggest that as was seen in vitro, the efficiency of CPT increases as virus dose is reduced.

TABLE 6

| VIRUS DILUTION | ROUTE | ADD-ITIONS | # DISEASED MICE[1] | AVG. SPLEEN WT. (g) |
|---|---|---|---|---|
| 1/500 | IP | — | 5/5 | 0.94 |
|  |  | CPT | 0/1* | 0.20 |
| 1/1000 | IP |  | 3/5 | 1.06 |
|  |  | CPT | 0/2* | 0.15 |
| NONE | IP | CPT | 0/5 | 0.10 |
| 1/500 | IV | — | 5/5 | 1.98 |
|  |  | CPT | 0/5 | 0.10 |
| 1/1000 | IV |  | 4/5 | 1.32 |
|  |  | CPT | 0/5 | 0.12 |
| NONE | IV | CPT | 0/5 | 0.10 |

1. Number of diseased mice/injected mice
*4/5 and 3/5 injected mice died within 24 hours of injection of causes unrelated to viral disease The data presented above in Examples 1 and 3 demonstrate that non-cytotoxic doses of CPT have a strong inhibitory effect on HIV replication. A one-hour treatment with CPT during HIV infection of H9 cells was sufficient to prevent 94–100% of HIV replication, as measured by RT activity in the culture media 7 days after infection. These concentrations of CPT were also sufficient to strongly inhibit HIV replication following cocultivation of small amounts of H9/IIIB chronically-infected cells with uninfected cells. Moreover, when larger numbers of H9/IIIB cells were cocultivated with uninfected cells, an increasing dose of CPT (0.2 $\mu$M) or, alternatively, a longer treatment period (18h) with a very low CPT dose (0.005 $\mu$M), resulted in a strong inhibitory effect on HIV replication. These results indicate that CPT inhibits HIV replication in a dose dependent manner, and acts as an antiviral drug at levels 400 times lower than those which produce a cytotoxic effect. The inhibitory effect of CPT and HIV replication seems to be specific, and not a general characteristic of topoisomerase inhibitors since topoisomerase II inhibitors such as m-AMSA and VP-16 do not have any significant effect on HIV replication (Example 2). Preliminary evidence also suggests that virus production is suppressed by non-cytotoxic doses of CPT in chronically HIV-infected cells. These results indicate that CPT may reduce HIV replication not only during de novo infection, but also in chronically-infected cells.

CPT inhibits Moloney MuLV replication in vitro and blocks the induction of erythroleukemia by SFFV in vivo. CPT also inhibits equine infectious anemia virus (EIAV) replication in chronically-infected cells, suggesting that it may act at a common, but as yet unknown, step in the life cycle of retroviruses.

In view of the fact that retroviruses possess their own unique topo I, that this topo I is inhibited by CPT, that CPT inhibits HIV infection and replication in H9 cells, that CPT blocks the spread of HIV in uninfected H9 cells cocultivated with cells chronically infected with HIV, and that CPT is effective in vivo as demonstrated by its inhibition of Friend virus disease initiation and spread in mice, the ordinary skilled artisan would reasonably expect CPT to be effective in the treatment of retroviral infections in humans.

A large number of agents which block HIV replication, such as reverse transcriptase inhibitors, block the early stages of the HIV infectious process, and CPT can be administered in cooperation with drugs of this type.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed:

1. A method for treating retroviral infections in a mammal, including humans, comprising administering to said mammal an anti-retroviral effective amount of a topoisomerase I inhibitor and an anti-retroviral effective amount of a compound selected from the group consisting of AZT, soluble CD4, and an interferon, or combinations of said latter compounds.

2. The method of claim 1, wherein said topoisomerase I inhibitor is camptothecin or a derivative thereof.

3. A pharmaceutical composition, comprising an anti-retroviral effective amount of a topoisomerase I inhibitor and an anti-retroviral effective amount of a compound selected from the group consisting of AZT, soluble CD4, and an interferon, or combinations of said latter compounds.

4. The pharmaceutical composition of claim 3, wherein said topoisomerase I inhibitor is camptothecin or a derivative thereof.

5. The method of claim 1, wherein said compound is AZT.

6. The method of claim 2, wherein said compound is AZT.

7. The pharmaceutical composition of claim 3, wherein said compound is AZT.

8. The pharmaceutical composition of claim 4, wherein said compound is AZT.

* * * * *